(12) United States Patent
Shimokawatoko et al.

(10) Patent No.: US 10,314,300 B2
(45) Date of Patent: Jun. 11, 2019

(54) METHOD FOR CONTROLLING ARTHROPOD PESTS

(71) Applicant: Sumitomo Chemical Company, Limited, Tokyo (JP)

(72) Inventors: Yasutaka Shimokawatoko, Takarazuka (JP); Ayako Hirao, Takarazuka (JP); Atsushi Iwata, Walnut Creek, CA (US)

(73) Assignee: Sumitomo Chemical Company, Limited, Tokyo (JP)

( * ) Notice: Subject to any disclaimer, the term of this patent is extended or adjusted under 35 U.S.C. 154(b) by 273 days.

(21) Appl. No.: 15/306,793

(22) PCT Filed: Apr. 20, 2015

(86) PCT No.: PCT/JP2015/061967
§ 371 (c)(1),
(2) Date: Oct. 26, 2016

(87) PCT Pub. No.: WO2015/166829
PCT Pub. Date: Nov. 5, 2015

(65) Prior Publication Data
US 2017/0055515 A1    Mar. 2, 2017

(30) Foreign Application Priority Data

Apr. 28, 2014    (JP) .................................. 2014-092359

(51) Int. Cl.
| | | |
|---|---|---|
| *A01N 25/00* | (2006.01) | |
| *A01N 51/00* | (2006.01) | |
| *A01N 59/26* | (2006.01) | |
| *A01M 17/00* | (2006.01) | |
| *A01M 1/20* | (2006.01) | |

(52) U.S. Cl.
CPC .............. *A01M 17/00* (2013.01); *A01M 1/20* (2013.01); *A01N 25/00* (2013.01); *A01N 51/00* (2013.01); *A01N 59/26* (2013.01)

(58) Field of Classification Search
CPC .......... A01M 17/00; A01M 1/20; A01M 1/00; A01N 25/00; A01N 51/00; A01N 59/26; A01N 29/00
See application file for complete search history.

(56) References Cited

U.S. PATENT DOCUMENTS

| | | | |
|---|---|---|---|
| 5,783,203 | A | 7/1998 | Schütte et al. |
| 2014/0020610 | A1 | 1/2014 | Sakamoto et al. |

FOREIGN PATENT DOCUMENTS

| | | |
|---|---|---|
| FR | 2984685 A1 | 6/2013 |
| JP | H10287502 A | 10/1998 |
| JP | 2013133308 A | 7/2013 |
| JP | 2014037401 A | 2/2014 |
| WO | 1995028370 A1 | 10/1995 |
| WO | 2003045877 A1 | 6/2003 |
| WO | 2005112624 A2 | 12/2005 |
| WO | 2010032871 A1 | 3/2010 |
| WO | 2013064461 A2 | 5/2013 |

OTHER PUBLICATIONS

Supplemental European Search Report dated Jan. 5, 2018 in EP Application No. 15785953.9.
Extended Search Report dated Dec. 11, 2017 in EP Application No. 15785953.9.
Int'l Search Report dated Jun. 30, 2015 in Int'l Application No. PCT/JP2015/061967 (English Translation).
Int'l Preliminary Report on Patentability dated Nov. 1, 2016 in Int'l Application No. JP/2015/061967 (English Translation).

*Primary Examiner* — Christopher J. Novosad
(74) *Attorney, Agent, or Firm* — Panitch Schwarze Belisario & Nadel LLP

(57) ABSTRACT

A method for controlling arthropod pests includes the following steps: A) a step of forming furrows in the soil; B) a step of sowing seeds of a crop in the furrows; C) a step of applying clothianidin and an inorganic phosphate to the furrows; and D) a step of covering the furrows by gathering soil into the furrows.

5 Claims, No Drawings

METHOD FOR CONTROLLING ARTHROPOD PESTS

CROSS-REFERENCE TO RELATED APPLICATION

This application is a Section 371 of International Application No. PCT/JP2015/061967, filed Apr. 20, 2015, which was published in the Japanese language on Nov. 5, 2015, under International Publication No. WO 2015/166829 A1, and the disclosure of which is incorporated herein by reference.

TECHNICAL FIELD

The present invention relates to a method for controlling arthropod pests, the method including a step of forming furrows in the soil, a step of sowing seeds of a crop in the furrows, a stop of applying clothianidin and an inorganic phosphate to the furrows, and a step of covering the furrows by gathering the soil into the furrows.

BACKGROUND ART

Various methods are conventionally known as the method for controlling arthropod pests, and the methods have been provided for practical use.

CITATION LIST

Non-Patent Literature

[NPL 1] Handbook of Corn Insects. ISBN: 0-938522-76-0., 1999, Entomological Society of America.

SUMMARY OF INVENTION

Technical Problem

For the purpose of coping with the global increase in population, a variety of efforts have been made to increase the yield of crops. However, since there is a significant decrease in the yield of crops caused by insect damages, there has been a demand for an excellent method for controlling arthropod pests that damage crops by feeding.

Solution to Problem

The inventors of the present invention conducted an investigation to find an excellent method for controlling arthropod pests, and as a result, the inventors found that arthropod pests can be controlled by forming furrows in the soil, sowing seeds of a crop in the furrows, applying clothianidin and an inorganic phosphate to the furrows, and covering the furrows by gathering the soil that were put to a side when the furrows were formed. Thus, the inventors completed the present invention.

That is, the present invention includes the following items [1] to [5].

[1] A method for controlling arthropod pests, the method comprising the following steps: A) a step of forming furrows in the soil; B) a step of sowing seeds of a crop in the furrows; C) a step of applying clothianidin and an inorganic phosphate to the furrows; and D) a step of covering the furrows by gathering soil into the furrows.

[2] The method for controlling arthropod pests according to [1], wherein the step C) is a step of applying a mixed composition containing clothianidin and an inorganic phosphate into the furrows.

[3] The method for controlling arthropod pests according to [1] or [2], wherein the inorganic phosphate is an ammonium phosphate.

[4] The method for controlling arthropod pests according to any one of [1] to [3], wherein the amount of application of clothianidin is 10 to 500 g per hectare.

[5] The method for controlling arthropod pests according to any one of [1] to [4], wherein the amount of application of the inorganic phosphate is 10 to 60 kg per hectare.

Advantageous Effects of Invention

An excellent controlling effect against arthropod pests can be obtained by the present invention.

DESCRIPTION OF EMBODIMENTS

The present invention includes: A) a step of forming furrows in the soil, B) a step of sowing seeds of a crop in the furrows, C) a step of applying clothianidin and an inorganic phosphate in the furrows, and D) a step of covering the furrows by gathering soil into the furrows. In the following explanation, the respective steps may be described in short forms such as Step (A), Step (B), Step (C), and Step (D).

The present invention includes A) a step of forming furrows in the soil. The furrows according to the present invention are linear pits formed in approximately flat soil in which a crop is cultivated. Usually, furrows are formed by using an agricultural implement such as a shovel or a hoe above the soil, or as a furrow-forming device installed in a machine such as a tractor moves horizontally above the soil. The shape of the furrows may vary depending on the agricultural implement or furrow-forming device to be used; however, furrows in which the cross-sectional shape in the direction perpendicular to a furrow is an inverse triangle are generally used.

The present invention includes B) a step of sowing seeds of a crop in the furrows. Sowing seeds of a crop in the furrows means that seeds are placed in the furrows formed in Step (A). Usually, seeds are placed in the furrows by the part for seeding of a seeding machine towed by a tractor. The part for seeding of a seeding machine is usually installed at the back of the part for forming furrows, and seeds are sowed in the furrows as the tractor moves. Examples of such a part include a mechanical seeder and a pneumatic seeder.

The present invention includes C) a step of applying clothianidin and an inorganic phosphate to the furrows. Clothianidin that is used for the present invention is a known compound and is described in, for example, page 225 of "The Pesticide Manual—16$^{th}$ Edition (published by BCPC); ISBN 978-1-901396-86-7". Clothianidin is obtained from a commercially available preparation, or is obtained by producing the compound by a known method.

Clothianidin that is used for the present invention may be the compound itself; however, usually, a form formulated into an arbitrary dosage form such as granules, a water-soluble powder, a wettable powder, water-dispersible granules, a soluble concentrate, microcapsules, an emulsifiable concentrate, a concentrated emulsion, a microemulsion, a suspoemulsion, an oil-miscible liquid, a suspension concentrate or a dry flowable, by mixing clothianidin with an appropriate solid carrier or liquid carrier, and adding a surfactant or other auxiliary agents for formulation to the mixture as necessary, is preferred.

Examples of the inorganic phosphate that is used for the present invention include salts of phosphate ion, monohydrogen phosphate ion, and dihydrogen phosphate ion with calcium ion, ammonium ion, magnesium ion, potassium ion and the like. Specific examples include calcium dihydrogen phosphate, dicalcium hydrogen phosphate, rhenanite, ammonium dihydrogen phosphate, diammonium hydrogen phosphate, ammonium polyphosphate, monomagnesium phosphate, dimagnesium phosphate, potassium dihydrogen phosphate, dipotassium hydrogen phosphate, tripotasium phosphate, and potassium pyrophosphate. The inorganic phosphate is preferably an ammonium phosphate.

The inorganic phosphate that is used for the present invention may be a salt itself; however, the inorganic phosphate may also be in the form of particles, a powder, lumps, a liquid, an aqueous solution, an aqueous dispersion or the like. An inorganic phosphate having an appropriate form is used according to the soil to which the inorganic phosphate is applied, or the implement used for the treatment.

In regard to (C) step of applying clothianidin and an inorganic phosphate in the furrows, clothianidin and the inorganic phosphate may be respectively applied alone in the forms described above, or may be applied in the form of a mixed composition containing clothianidin and the inorganic phosphate.

The mixed composition containing clothianidin and an inorganic phosphate may be a simple mixture of clothianidin and an inorganic phosphate; however, usually, the mixed composition is formulated by mixing clothianidin and an inorganic phosphate with an appropriate solid carrier or liquid carrier, and adding a surfactant or other auxiliary agents for formulation to the mixture as necessary. Examples of the dosage form include arbitrary dosage forms such as granules, a water-soluble powder, a wettable powder, water-dispersible granules, a soluble concentrate, and a suspension concentrate.

Examples of the solid carrier that is used at the time of formulating a preparation containing clothianidin and a mixed composition containing clothianidin and an inorganic phosphate, include natural or synthetic minerals such as clay, kaolin, talc, bentonite, sericite, sulfur, activated carbon, calcium carbonate, diatomaceous earth, quartz, pumice, calcite, sepiolite, dolomite, olivine, pyroxene, amphibole, feldspar, silica, alumina, vermiculite, and pearlite; and fine particles of elastomers, plastics, ceramics, metals, sawdust, corncobs, coconut husks, and tobacco stems. These can also be used as mixtures.

Examples of the liquid carrier include water, xylene, methanol, butanol, pentanol, benzyl alcohol, cyclohexanone, γ-butyrolactone, N-methylpyrrolidone, N-octylpyrrolidone, glycol diacetate, glycols, fatty acid dimethyl amides, fatty acids, and fatty acid esters. These can also be used as mixtures.

Examples of the surfactant include conventional nonionic surfactants, cationic surfactants, anionic surfactants and amphoteric surfactants, and one kind or two or more kinds of these are used.

Examples of such surfactants include alkyl sulfates, alkyl sulfuric acid ester salts, alkyl sulfonates, alkyl aryl sulfonates, lignin sulfonates, naphthalene sulfonates, phenol sulfonates, dibutyl naphthalene sulfonates, fatty alcohol sulfates, fatty acid alkyl aryl ethers and polyoxyethylene compounds thereof, polyethylene glycol ethers, polyethylene glycol fatty acid esters, polyhydric alcohol esters, sugar alcohol derivatives, and silicone-based surfactants.

Examples of the other auxiliary agents for formulation include emulsifiers such as nonionic emulsifiers and anionic emulsifiers (for example, polyoxyethylene fatty alcohol ether, an alkyl sulfonate, and an aryl sulfonate); dispersants such as a lignin sulfite waste liquid and methyl cellulose; antifoaming agents based on silicons or magnesium stearate; stabilizers such as PAP (acidic isopropyl phosphate) and BHT (butyl hydroxytoluene); antiseptic agents such as 5-chloro-2-methyl-4-isothiazolin-3-one, 1,2-benzothiazolin-3-one, and 2-bromo-2-nitropropane-1,3-diol; coloring materials such as red colors (for example, Monazol Red), blue colors (for example, Prussian Blue and Brilliant Blue), and green colors (for example, Cyanine Green); and antifreezes such as glycerin, ethylene glycol, and propylene glycol.

In a case in which granules are used for the present invention, the granules are usually applied as received, without being dissolved in a solvent. The granules may be processed into forms such as fine granules, macrogranules, and microgranules, by varying the particle size of the granules.

The content of clothianidin in the granules containing clothianidin is usually 0.01% to 10% by weight, preferably 0.1% to 5% by weight, and more preferably 0.2% to 2% by weight, relative to the total weight of the granules.

The content of the solid carrier in the granules containing clothianidin is usually 10% to 99.99% by weight, and preferably 60% to 99.8% by weight, relative to the total weight of the granules, and in a case in which the granules contain a surfactant, the content of the surfactant is usually 1% to 20% by weight, and preferably 1% to 15% by weight, relative to the total weight of the granules.

Furthermore, in a case in which the mixed composition containing clothianidin and the inorganic phosphate is in the form of granules, the content of clothianidin in the granules is usually 0.01% to 10% by weight, preferably 0.1% to 5% by weight, and more preferably 0.2% to 2% by weight, relative to the total weight of the granules, and the content of the inorganic phosphate is usually 10% to 99.9% by weight, and preferably 40% to 99.8% by weight, relative to the total weight of the granules.

According to the present invention, in the case of using a water-soluble powder, a wettable powder, water-dispersible granules, a soluble concentrate, microcapsules, an emulsifiable concentrate, a concentrated emulsion, a microemulsion, a suspoemulsion, an oil-miscible liquid, a suspension concentrate or a dry flowable, usually, an aqueous dispersion or an aqueous solution obtainable by dispersing or dissolving any one of the preparations described above in water is applied.

The form of application of the aqueous dispersion or the aqueous solution is not particularly limited; however, particularly spraying, dripping or drenching is preferred. Clothianidin and the inorganic phosphate may be applied separately, or may also be applied as a mixture.

The amount of application of the aqueous dispersion or the aqueous solution may vary as appropriate depending on the conditions for cultivation or crops, climate conditions, etc.; however, the amount is usually 10 to 1200 liters, preferably 50 to 500 liters, and more preferably 50 to 300 liters, per hectare.

In regard to C) step of applying clothianidin and an inorganic phosphate to the furrows, applying clothianidin and an inorganic phosphate to the furrows implies that clothianidin granules or microgranules and an inorganic phosphate, or granules or microgranules containing clothianidin and an inorganic phosphate are placed or scattered in the furrows formed for sowing seeds of a crop, or an aqueous dispersion or an aqueous solution containing clothianidin, an aqueous dispersion or an aqueous solution containing an inorganic phosphate, or an aqueous dispersion or an aqueous solution containing clothianidin and an inorganic phosphate is sprayed, dripped or drenched to the furrows formed for sowing seeds of a crop.

According to the present invention, usually, Step (B) is carried out after Step (A), subsequently Step (C) is carried out, and Step (D) is carried out at the last. Alternatively, Step (C) is carried out after Step (A), subsequently Step (B) is carried out, and Step (D) is carried out at the last.

Step (C) may include: C1) a step of applying clothianidin to the furrows (hereinafter, described briefly as Step (C1)), and C2) a step of applying an inorganic phosphate to the furrows (hereinafter, described briefly as Step (C2)). Step (C2) may be carried out after Step (C1), or Step (C1) may be carried out after Step (C2). Furthermore, the processes may be carried out in the order of Step (C1), Step (B), and Step (C2), or may be carried out in the order of Step (C2), Step (B), and Step (C1).

Usually, A) step of forming furrows in the soil, B) step of sowing seeds of a crop in the furrows, and C) step of applying clothianidin and an inorganic phosphate to the furrows are carried out, and then immediately the D) step of covering the furrows by gathering soil into the furrows is carried out by covering the furrows with the soil that has been put to a side at the time of forming the furrows.

According to the present invention, the amounts of application of clothianidin and the inorganic phosphate may be varied as appropriate depending on the conditions for cultivation of crops, climate conditions, etc.; however, the amount of application of clothianidin is usually 5 to 700 g, and preferably 10 to 500 g, per hectare, and the amount of application of the inorganic phosphate is usually 1 to 100 kg, and preferably 10 to 60 kg, per hectare.

The present invention relates to a method for controlling arthropod pests that damage the seeds sowed in Step (B) and the plants grown from the seeds, by performing the Steps (A) to (D).

According to the present invention, since clothianidin is efficiently absorbed through the roots of a crop grown in a furrow, and penetrates and migrates throughout the entire crop, the insecticidal effect of clothianidin is exhibited against arthropod pests that eat away and sap the crop. Specific examples of the arthropod pests, that is, the pests that can be controlled by the present invention, include the following.

Hemipteran pests: planthoppers such as *Laodelphax striatellus*; leafhoppers such as *Empoasca onukii*, aphids such as *Aphis gossypii, Myzus persicae, Brevicoryne brassicae, Macrosiphum euphorbiae, Aulacorthum solani, Rhopalosiphym padi, Aphis naturtii*, and *Aphis fabae*; pentatomids such as *Nezara viridula* and *Lygus lineolaris*; and whiteflies such as *Bemisia tabaci* and *Bemisia argentifolii*.

Lopidopteran pests: pyralids such as *Ostrinia furnacalis* and *Ostrinia nubilaris*; noctuids such as *Spodoptera litura, Mythimna separata*, and *Agrotis ipsilon*; pierid butterflies such as *Pieris rapae*; ermine moths such as *Plutella xylostella*; and glechiids such as *Phthorimaea operculella*.

thysanopteran pests: thrips such as *Frankliniella occidentalis, Scirtothrips dorsalis, Thrips tabaci*, and *Frankliniella fusca*.

Dipteran pests: anthomylid flies such as *Delia platura* and *Delia antiqua*; and leafminer flies such as *Liriomyza sativae* and *Liriomyza trifolii*.

Coleopteran pests: corn rootworms (*Diabrotica* spp.) such as *Diabrotica virgifera virgifera* and *Diabrotica undecimpunctata howardi*; leaf beetles such as *Aulacophora femoralis* and *Leptinotarsa decemlineata*; and click beetles (*Agriotes* spp.).

The present invention is preferably applicable as a method for controlling *Agriotes* spp., *Diabrotica* spp., noctuids, anthomylid flies, and aphids.

Examples of the crops directly damaged by insects, that is, the crops to which the present invention can be applied include corn, wheat family (wheat, barley, rye, oat, and the like), soybean, rapeseed, sugar beet, rice, cotton, peanut, sunflower, sugar cane, tabacco, sorghum, and potato.

Among the crops described above, corn, soybean, potato, wheat family, and sorghum are preferred; corn or soybean is more preferred; and corn is most preferred.

The aforementioned crops may be crops imparted with resistance to herbicides, resistance to harmful pests, or resistance to environmental stress, by a genetic recombination technology or a classical breeding method based on crossbreeding.

EXAMPLES

Next, Formulation Examples and Test Examples related to the present invention will be described; however, the present invention is not intended to be limited to these Examples. Meanwhile, in the following Examples, the unit parts represent parts by weight, unless particularly stated otherwise.

<Production Example for Preparation Containing Clothianidin>

Reference Example 1 (Clothianidin Granules)

0.5 parts of clothianidin, 1 part of synthetic hydrated silicon oxide, 2 parts of calcium lignin sulfonate, 30 parts of bentonite, and 66.5 parts of kaolin clay are thoroughly pulverized and mixed, and water is added thereto. The mixture is thoroughly kneaded and then is granulated and dried. Thus, granules are obtained.

Reference Example 2 (Clothianidin Wettable Powder)

20 parts of clothianidin, 3 parts of sodium dodecyl benzene sulfonate, 3 parts of sodium lignin sulfonate, and 70 parts of diatomaceous earth are pulverized with a jet air mill, and thus a wettable powder is obtained.

<Production Example for Preparation Containing Clothianidin and Inorganic Phosphate>

Reference Example 3 (Mixed Wettable Powder of Clothianidin and Diammonium Hydrogen Phosphate)

0.5 parts of clothianidin, 40 parts of a diammonium hydrogen phosphate powder, 3 parts of sodium dodecyl benzene sulfonate, 3 parts of sodium lignin sulfonate, and 53.5 parts of diatomaceous earth are pulverized with a jet air mill, and thus a wettable powder is obtained.

<Production Example for Preparation Containing Inorganic Phosphate>

Reference Example 4 (Ammonium Dihydrogen Phosphate Granules)

100 parts of a mixture including 60 parts of an ammonium dihydrogen phosphate powder, 2 parts of calcium lignin sulfonate, 30 parts of bentonite, and kaolin clay for the balance is thoroughly pulverized and mixed, and water is added thereto. The mixture is thoroughly kneaded, and then is granulated and dried. Thus, granules are obtained.

Test Example 1

Preparation of Mixed Liquid

An aqueous solution containing 0.004% of clothianidin and 5% of diammonium hydrogen phosphate (hereinafter, described as present preparation liquid) was produced using a clothianidin water dispersible granule (used a 16% water dispersibie granule, trade name: DANTOTSU water soluble powder, manufactured by Sumitomo Chemical Co., Ltd.) and diammonium hydrogen phosphate (manufactured by Sigma-Aldrich Company).

Method of Using Mixed Liquid

1. A container having a diameter of 12 cm was filled with soil, and furrows were produced to a depth of 4 cm from the soil surface. 10 ml of the present preparation liquid was sprayed into the furrows, and one grain of corn seed (variety name: Mas53B) was sowed in each furrow. The furrows were covered by gathering soil from a side of each furrow. Corn was grown in a greenhouse. Fourteen days after sowing of the corn seeds, ten 3-instar larvae of *Mythimna separata* were released per stem of corn. This is referred to as a seeding furrow treatment section.

2. Similarly to the seeding furrow treatment section, a container was filled with soil, and 10 ml of the present preparation liquid was sprayed over the entire surface of the soil and was mixed with the entire soil. Subsequently, furrows were produced to a depth of 4 cm from the soil surface, and one grain of corn seed (variety name: Mas53B) was sowed in each furrow. The furrows were covered by gathering soil from a side of each furrow. Corn was grown in a greenhouse. Fourteen days after sowing of the corn seeds, ten 3-instar larvae of *Mythimna separata* were released per stem of corn. This is referred to as a soil incorporation treatment section.

3. Similarly to the seeding furrow treatment, a container was filled with soil, and furrows were produced to a depth of 4 cm from the soil surface. One grain of corn seed (variety name: Mas53B) was sowed in each furrow, and the furrows were covered by gathering soil from a side of each furrow. 10 ml of the present preparation liquid was sprayed over the entire soil surface in the container. Fourteen days after sowing of the corn seeds, ten 3-instar larvae of *Mythimna separata* were released per stem of corn. This is referred to as a soil surface drenching treatment section.

4. Similarly to the seeding furrow treatment, a container was filled with soil, and furrows were produced to a depth of 4 cm from the soil surface. One grain of corn seed (variety name: Mas53B) was sowed in each furrow, and the furrows were covered by gathering soil from a side of each furrow. Fourteen days after sowing of the corn seeds, ten 3-instar larvae of *Mythimna separata* were released per stem of corn. This is referred to as a chemically untreated section.

For each of the treated sections of 1, to 4, the numbers of healthy insects, moribund insects and dead insects of released *Mythimna separata* were investigated two days after the insect release, and the rate of dead or moribund insects was calculated using the following expression. For each of the treated sectiones, the average rate of dead or moribund insects of five tests is indicated in Table 1.

Rate of dead or moribund insects=100×(10−A)/10

A: Number of healthy insects at the time of investigation

TABLE 1

| | Treating chemical | Amount of treating chemical (mg/pot) | Rate of dead or moribund insects |
|---|---|---|---|
| Chemically untreated section | — | — | 4% |
| seeding furrow treatment section | Clothianidin<br>Diammonium hydrogen phosphate | 0.4<br>500 | 82% |
| soil incorporation treatment section | Clothianidin<br>Diammonium hydrogen phosphate | 0.4<br>500 | 42% |
| Soil surface drenching treatment section | Clothianidin<br>Diammonium hydrogen phosphate | 0.4<br>500 | 12% |

As a result, the seeding furrow treatment section exhibited a high rate of dead or moribund insects, compared to the chemically untreated section, the soli incorporation treatment section, and the soil surface drenching treatment section.

Test Example 2

Production of Mixed Liquid

An aqueous solution containing 0.004% of clothianidin and 5% of diammonium hydrogen phosphate was produced using a clothianidin water dispersibie granule (used a 16% water dispersibie granule, trade name: DANTOTSU water soluble powder, manufactured by Sumitomo Chemical Co., Ltd.) and diammonium hydrogen phosphate (manufactured by Sigma-Aldrich Company).

An aqueous solution containing 0.004% of clothianidin and 5% of ammonium chloride was produced using a clothianidin water dispersible granule (used a 16% water dispersible granule, trade name: DANTOTSU water soluble powder, manufactured by Sumitomo Chemical Co., Ltd.) and ammonium chloride (manufactured by Wako Pure Chemical Industries, Ltd.).

Method for Applying Mixed Liquid

1. A container having a diameter of 12 cm was filled with soil, and furrows were produced to a depth of 4 cm from the soil surface. 10 ml of the mixed liquid of clothianidin and diammonium hydrogen phosphate thus produced was sprayed into the furrows, and one grain of corn seed (variety name: Mas53B) was sowed in each furrow. The furrows were covered by gathering soil from a side of each furrow. Corn was grown in a greenhouse. Thirteen days after sowing of the corn seeds, seven 5-instar larvae of *Mythimna separata* were released per stem of corn. This is referred to as an ammonium phosphate treated section.

2. A container having a diameter of 12 cm was filled with soil, and furrows were produced to a depth of 4 cm from the soil surface. 10 ml of the mixed liquid of clothianidin and ammonium chloride thus produced was sprayed into the furrows, and one grain of corn seed (variety name: Mas53B) was sowed in each furrow. The furrows were covered by gathering soil from a side of each furrow. Corn was grown in a greenhouse. Thirteen days after sowing of the corn seeds, seven 5-instar larvae of *Mythimna separata* were released per stem of corn. This is referred to as an ammonium chloride treated section.

3. A container having a diameter of 12 cm was filled with soil, and furrows were produced to a depth of 4 cm from the soil surface. One grain of corn seed (variety name: Mas53B) was sowed in each furrow, and the furrows were covered by gathering soil from a side of each furrow. Corn was grown in a greenhouse. Thirteen days after sowing of the corn seeds, seven 5-instar larvae of *Mythimna separata* were released per stem of corn. This is referred to as a chemically untreated section.

The numbers of healthy insects, moribund insects and dead insects of released *Mythimna separata* were investigated one day after the insect release, and the rate of dead or moribund insects was calculated using the following expression. For each of the treated sections, the average rate of dead or moribund insects of five tests was determined. The results are presented in Table 2.

Rate of dead or moribund insects=$100 \times (7-A)/7$

A: Number of healthy insects at the time of investigation

TABLE 2

| Treating chemical | | Amount of treating chemical (mg/pot) | Rate of dead or moribund insects |
|---|---|---|---|
| Chemically untreated section | — | — | 0% |
| Ammonium phosphate treated section | Clothianidin | 1.2 | 83% |
| | Diammonium hydrogen phosphate | 500 | |

TABLE 2-continued

| Treating chemical | | Amount of treating chemical (mg/pot) | Rate of dead or moribund insects |
|---|---|---|---|
| Ammonium chloride treated section | Clothianidin | 1.2 | 49% |
| | Ammonium chloride | 500 | |

As a result, the ammonium phosphate treated section exhibited a high rate of dead or moribund insects, compared to the ammonium chloride treated section.

INDUSTRIAL APPLICABILITY

An excellent controlling effect against arthropod pests can be obtained by the present invention.

The invention claimed is:

1. A method for controlling arthropod pests, the method comprising the following steps:
   A) a step of forming furrows in the soil;
   B) a step of sowing seeds of a crop in the furrows;
   C) a step of applying clothianidin and an inorganic phosphate to the furrows; and
   D) a step of covering the furrows by gathering soil into the furrows.

2. The method for controlling arthropod pests according to claim 1, wherein the step C) is a step of applying a mixed composition containing clothianidin and an inorganic phosphate to the furrows.

3. The method for controlling arthropod pests according to claim 1, wherein the inorganic phosphate is an ammonium phosphate.

4. The method for controlling arthropod pests according to claim 1, wherein the amount of application of clothianidin is 10 to 500 g per hectare.

5. The method for controlling arthropod pests according to claim 1, wherein the amount of application of the inorganic phosphate is 10 to 60 kg per hectare.

* * * * *